United States Patent [19]

Takada et al.

[11] Patent Number: 4,937,451
[45] Date of Patent: Jun. 26, 1990

[54] COMPUTED TOMOGRAPH

[75] Inventors: Michinosuke Takada; Shun-ichiro Sasaki, both of Ukyo, Japan

[73] Assignee: Shimadzu Corporation, Japan

[21] Appl. No.: 321,357

[22] Filed: Mar. 10, 1989

[30] Foreign Application Priority Data

Mar. 29, 1988 [JP] Japan .............................. 63-42251[U]
Apr. 30, 1988 [JP] Japan .............................. 63-58886[U]

[51] Int. Cl.$^5$ ................................................ A61B 5/00
[52] U.S. Cl. ............................... 250/358.1; 250/359.1; 250/360.1; 250/453.1
[58] Field of Search ............... 250/358.1, 359.1, 360.1, 250/453.1

[56] References Cited

U.S. PATENT DOCUMENTS

| | | | |
|---|---|---|---|
| 3,974,388 | 8/1976 | Distler et al. | 378/20 |
| 4,131,802 | 12/1978 | Braden et al. | 378/20 |
| 4,688,278 | 8/1987 | Van Aspert | 5/81 B |
| 4,767,928 | 8/1988 | Nelson et al. | 250/341 |
| 4,773,029 | 9/1988 | Claesson et al. | 364/562 |

FOREIGN PATENT DOCUMENTS 0255645 7/1987 European Pat. Off. .
8801485 3/1988 PCT Int'l Appl. .

OTHER PUBLICATIONS

Robert H. Lenon, O. P. Gandhi, James L. Meyerhoff and H. Mark Grove, "A Microwave Applicator for In Vivo Rapid Inactivation of Enzymes in the Central Nervous System," *IEEE Transactions on Microwave Theory* (Jan. 1976) pp. 58–61.
Unexamined Japanese Patent Application No. 60-72542 (4-1985).

*Primary Examiner*—Constantine Hannaher
*Attorney, Agent, or Firm*—Fidelman & Wolffe

[57] ABSTRACT

In a computed tomograph wherein an object to be examined is scanned with a beam of light in a scanning plane and a photodetector receives the light transmitted through the object so that a tomographic image of the object is obtained, there is provided a holder for holding the object in the scanning plane, which comprises two separate portions arranged at the opposite sides of the scanning plane, each of the two separate portions having a supporting surface at substantially the same level for supporting at least a portion of the object being examined.

6 Claims, 5 Drawing Sheets

COMPUTED TOMOGRAPH

BACKGROUND OF THE INVENTION

This invention relates generally to computed tomographs commonly referred to as CT's for nondestructively obtaining a tomographic information of an object being examined by employing radiation, and more particularly to a device for holding an object to be examined in computed tomographs.

X-ray CT's are commonly used for nondestructively obtaining a tomographic information of an object to be examined. There has been proposed a CT of such a type that obtains a tomographic information of an object by irradiating the object with light in the visible and near infrared regions as disclosed in, for example, Japanese Unexamined Patent Publication No. 60-72542.

The apparatus generally includes a light beam scanning device which comprises scanning means for causing the light beam from a source to transmit through different parts of an object to be examined, and a photodetector opposite the scanning means to receive the light emitted by the scanning means and transmitted through the object.

The disclosed CT is schematically shown in FIGS. 5 and 6. FIG. 5 is a side elevational view, partly broken away, of the apparatus and FIG. 6 is a sectional view taken along line A—A in FIG. 5.

The apparatus comprises a gantry 1 in the form of a cylindrical drum, which is rotatably supported at the outer circumferential surface 1c thereof by means of rollers 2. An object 3 to be examined is placed adjacent the axis X of the gantry 1.

The gantry is formed on the entire circumferential surface 1c thereof with a screw groove, not shown, which is engaged by a gear not shown but driven by a motor to rotate the gantry about its axis X.

Inside the gantry there are provided a light source 5 for emitting a beam 6 of light, a reflector 7 for directing the light beam 6 onto the object 3 to be scanned and a scanner 8 for swinging the reflector 7 so that the beam 6 scans a sector-shaped range through an angle θ sufficient to cover the area of the object 3 to be examined.

The light source 5, the reflector 7 and the scanner 8 constitute the previously mentioned beam scanning means.

Inside the gantry, there is also provided a photodetector 9 at the side of the object opposite the reflector 7 and at such a position as to be able to receive the light beam 6 that has scanned the object 3. The photodetector 9 comprises a plurality of photosensitive elements arranged along an arc of a circle whose center coincides with a point at the surface of the reflector 7. The photodetector can be a photodiode array or a plurality of optical fibers each having one end arranged along the above-mentioned arc and the opposite end connected to a photomultiplier tube not shown.

With an object 3 to be examined being set in place and the gantry 1 kept stationary, the reflector 7 is swung so as to cause the light beam 6 to scan the sector-shaped range of the angle θ. Then the gantry 1 is rotated a predetermined angle and kept stationary and the light beam 6 is caused to scan in a similar manner. By repeating the above-mentioned rotation of the gantry 1 and scanning of the object by the light beam 6 it is possible to successively change the direction of incidence of the light beam on an object being examined at predetermined intervals circumferentially of the object and scan the object in all directions through 360°.

Inside the gantry 1 the object 3 is held by a holder, a typical example of which is shown in FIG. 7 in the form of a hollow cylinder 4 made of transparent glass. The beam 6 scans in a plane (to be referred to as the scanning plane) perpendicular to the axis of the cylindrical holder 4 as shown in FIG. 8, that is, in parallel with the plane of the drawing sheet. So long as the scanning light beam 6 passes adjacent the center of the cylinder of the holder 4, there is no problem. As the light beam swings toward the periphery of the cylinder, the incident angle α of the light beam on the cylinder comes to exceed a certain angle, whereupon the light beam cannot pass through the cylinder wall but is reflected as shown at 6a in FIG. 8, so that measurement becomes impossible.

If the diameter of the holder 4 is made of a larger size than the sector-shaped area scanned by the light beam as shown in FIG. 9, the position of the object 3 would be lowered out of the scanning area as the light source is moved about the holder 4, with resulting impossibility of measurement.

SUMMARY OF THE INVENTION

Accordingly, the primary object of the invention is to provide a device for holding an object to be examined in a CT, in which the holder comprises two parts disposed at the opposite sides of the scanning plane of the light beam, with a mechanism for moving the object being examined in a direction perpendicular to the scanning plane of the light beam.

With an object to be examined placed on the holder in such a manner that the object bridges the two parts of the holder, as the light beam scans the object, the beam passes through the object only between the two parts of the holder.

When the gantry is rotated to change the direction of incidence of the scanning light beam circumferentially of the object holder, the holder will not obstruct the light beam passing through the object being examined. To examine a different part of the object the holder is moved to shift the position of the object in a direction perpendicular to the scanning plane.

PREFERRED EMBODIMENTS OF THE INVENTION

Figure 1:
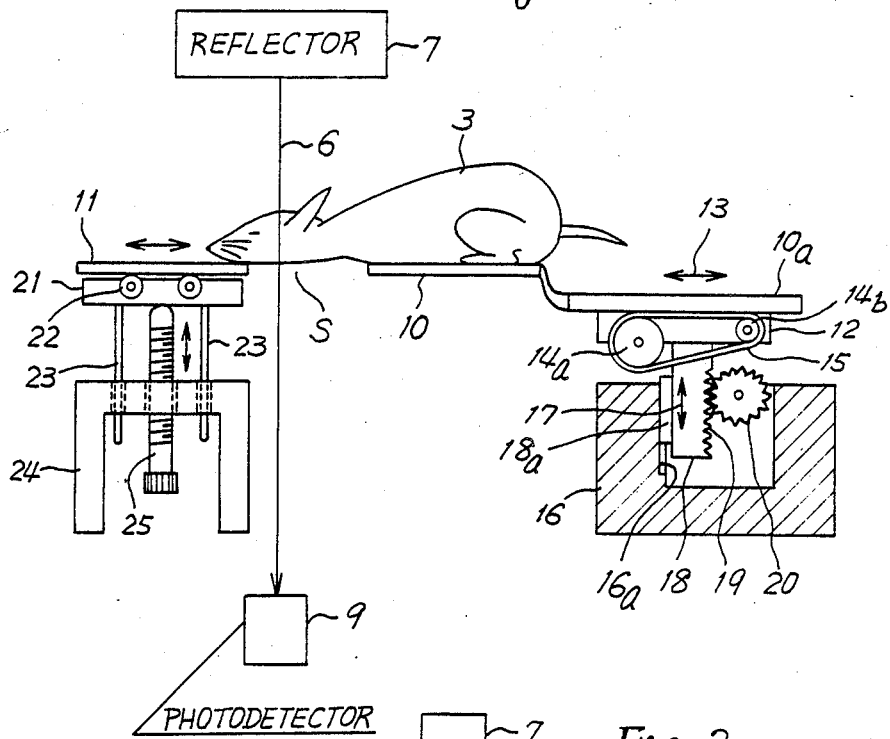
FIG. 1 is a schematic elevational view, partly in vertical section, of one embodiment of the invention.
Figure 2:
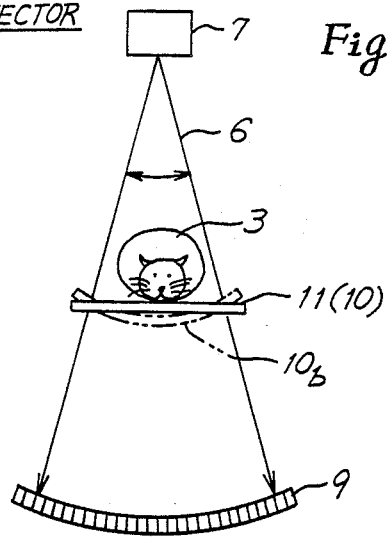
FIG. 2 is a schematic side view of FIG. 1 illustrating the relative positions of a scanning light beam, an object being examined, a holder for holding the object being examined and a photodetector.

FIG. 1 shows one embodiment of the invention, and FIG. 2 is a left side view schematically showing a reflector mirror 7, an object 3 being examined, an object holder comprising a pair of holding plates 10 and 11, and a photodetector 9.

The plates 10 and 11 are positioned at substantially the same level with a space S interposed therebetween. The object 3 to be examined, such as a rat, is placed on the plates 10 and 11 so as to bridge them. The reflector 7 above the space S reflects the light from a light source not shown so that the reflected light beam 6 passes through the space S so as to be projected onto the photodetector 9. As the reflector is swung, the light beam 6 scans the object 3 in a direction perpendicular to the plane of the drawing sheet of FIG. 1. The reflector 7 may be replaced by the light source, which may be swung so that the light beam from the source scans the object.

The holding plate 10 is connected to a movable member 10a integrally therewith. The movable member 10a with the holding plate 10 is supported by a support plate 12 so as to be movable horizontally as shown by an arrow 13. The support plate 12 is provided with a sprocket wheel 14a driven by a motor not shown, with a chain 15 passing about the sprocket wheel 14a and another sprocket wheel 14b. The movable member 10a is fixed to the chain 15, so that as the sprocket wheel 14a is rotated by the motor, the chain 15 moves the movable member 10a and the holding plate 10.

To the bottom face of the support plate 12 there is fixed a member 18 having a key 18a guided in a groove 16a formed in a base 16 so that the member 18 is movable in a vertical direction as shown by an arrow 17. The member 18 is formed with a rack 19 with which a drive gear 20 driven by a motor not shown meshes.

The other holding plate 11 is supported on a support plate 21 by means of bearing means such as rollers 22 so that the holding plate 11 is movable on the support plate 21 smoothly with reduced friction.

The support plate 21 is supported on the top end of a screw rod 25 threaded through a base 24, with guide rods 23 depending from the support plate 21 to pass through holes formed in the base 24. By rotating the screw rod 25 it is possible to raise or lower the support plate 21 and the holding plate 11.

In operation, an object 3 to be examined is set on the holder in such a manner that the object bridges the two holding plates 10 and 11, with the part of the object to be measured being positioned in the space S, through which the scanning light beam 6 passes. In the space S there is present nothing but the part of the object to be measured, so that no account need be taken of adverse influence of reflection or refraction of light by the holder or any other obstacles on the result of measurement.

To measure a different part of the object 3, the moving mechanism including the chain 15 and the sprocket wheels 14a and 14b is operated to shift the holding plate 10 in the direction in which the object is to be shifted, whereupon the other holding plate 11 is pulled or pushed by the friction between the plate 11 and the object 3 thereon so as to move in the same direction as the holding plate 10, with the width of the space S being kept substantially unchanged.

By temporarily fixing the object 3 to the holding plate 11 by suitable means such as an adhesive tape it is possible to effectively prevent the object from inadvertently falling off the holder when it is shifted.

When an object of a different size is placed on the holder, the positions of the holding plates 10 and 11 are adjusted vertically so as to set the part of the object to be measured at the center of the scanning range of the light beam 6.

The position of the object 3 illustrated in FIG. 1 is for obtaining a tomographic image of the object. To obtain a CR image, that is, a plane image like an ordinary X-ray picture, the gantry 1 is not rotated, but the reflector 7 (or the light source in place of the reflector) is swung and the holding plate 10 is moved in a horizontal direction. If the holding plate 10 is made of a material such as glass transparent to the scanning light, the object 3 may be placed on the holding plate 10 only without bridging the plates 10 and 11. In this case, although the holding plate 10 as well as the object 3 thereon is positioned within the scanning range of the light beam 6, it is possible to measure the object without being obstructed by the holding plate 10, and the other holding plate 11 and the associated members may be removed from their operative positions.

The material of the holding plate 10 is preferably transparent to the scanning light to make it possible to obtain a CR image. The material of the plate 10 may be nontransparent if tomographic images only are to be obtained.

In the embodiment of FIG. 1, the holding plate 10 is flat. It may be slightly curved as shown at 10b in FIG. 2 to reduce the influence of refraction if the holding plate 10 of a transparent material as well as the object to be measured is placed in the scanning area of the light beam 6 to obtain a CR image of the object.

The holding plates 10 and 11 may be a hollow cylinder or a box made of a material nontransparent to the scanning light so as to shut off any interfering light other than the scanning light.

Figure 3:
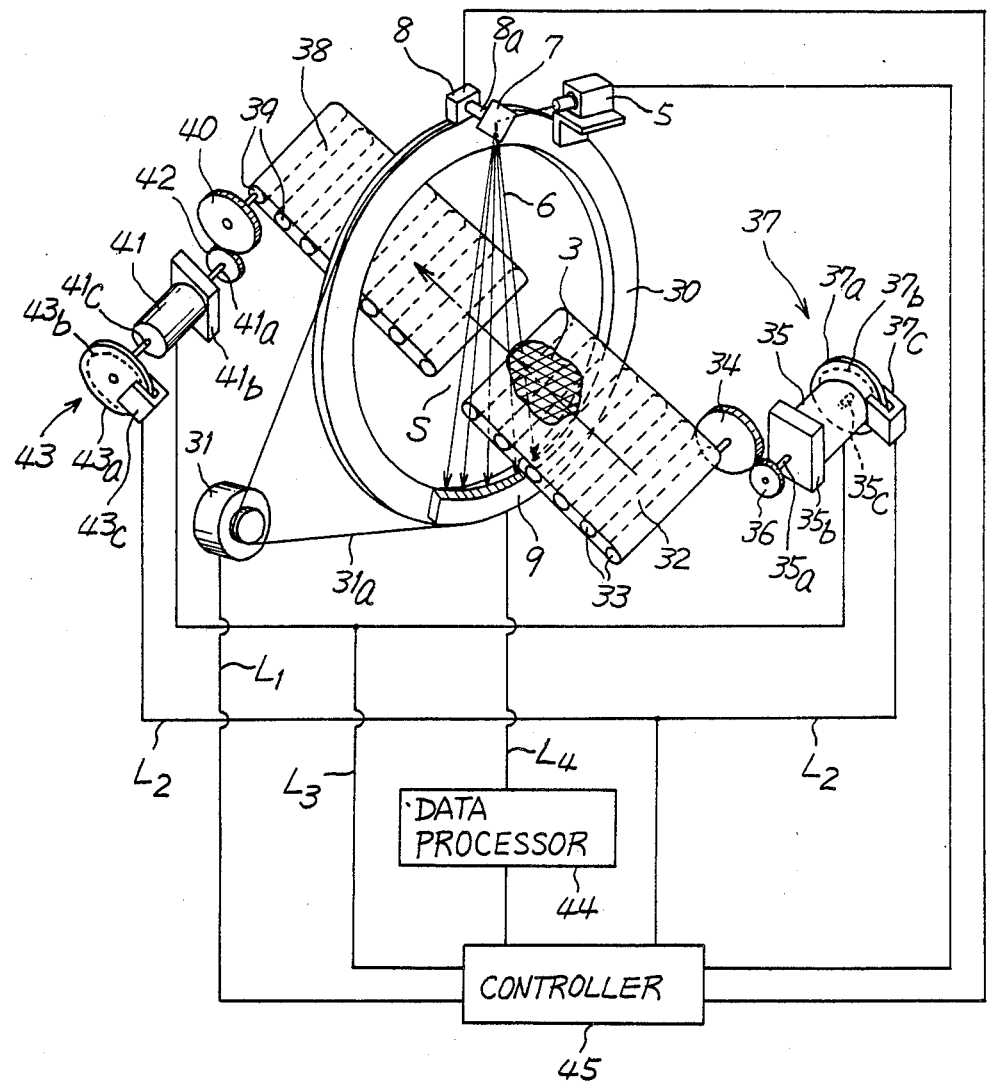
FIG. 3 is a schematic perspective view of another embodiment of the invention.

FIG. 3 shows a second embodiment of the invention, which comprises an annular gantry 30 provided with a light source 5, a scanner 8 and a photodetector 9. The scanner 8 has a rotatable shaft 8a on which a reflector 7 is mounted so that the reflected light beam from the reflector 7 swings so as to be projected onto the photodetector 9. The light source 5 can be a laser which emits light in the near infrared region. On the gantry 30 the photodetector 9 is positioned diametrically opposite the reflector 7 so that the photodetector 9 may catch all the light from the reflector 7. A motor 31 rotates the gantry through a belt 31a. A line $L_1$ supplies power to the motor 31.

At one side of the scanning plane of the light beam 6 and in front of the annular gantry 30 there is provided means for introducing an object 3 to be examined into the scanning region of the light beam 6. The introducing means comprises a plurality of parallel rollers 33, and endless conveyor belt 32 running on the rollers 33, and a motor 35 for driving the conveyor belt 32 via a gear 36 fixed to the output shaft 35a of a reduction gear 35b connected to the motor and a gear 34 fixed to one of the rollers 33 and meshing with the gear 36.

A position detector 37 is provided to detect the position of the conveyor belt 32 as it runs, and comprises a disc 37a fixed to the output shaft 35c of the motor 35 and provided with marks 37b circumferentially arranged on the disc 37a and a photosensor 37c for sensing each of the marks 37b to produce a corresponding detection signal on an output line L₂.

An object 3 to be examined is placed on the conveyor belt 32.

At the other side of the scanning plane of the light beam 6 and at the back of the gantry 30 there is provided means for receiving and holding the object 3, which comprises a plurality of parallel rollers 39 at the same level as the rollers 33, an endless conveyor belt 38 running on the rollers 39, and a motor 41 for driving the conveyor belt 38 via a gear 42 fixed to the output shaft 41a of a reduction gear 41b connected to the motor 41 and a gear 40 fixed to one of the rollers 39 and meshing with the gear 42. Another position detector 43 is provided to detect the position of the conveyor belt 38 as it runs, and comprises a disc 43a fixed to the output shaft 41c of the motor 41 and provided with marks 43b circumferentially arranged on the disc 43a and a photosensor 43c for sensing each of the marks 43b to produce a corresponding detection signal on the output line L₂.

The two motors 35 and 41 are rotated at substantially the same speed, with a line L₃ supplying power to the motors.

The distance between the adjacent ends of the conveyor belts 32 and 38 or the width of the space S may be several tens millimeters.

In operation, as the motors 35 and 41 are rotated at the same speed, the forward end of an object 3 placed on the conveyor belt 32 passes the space S between the belts 32 and 38 in which the scanning plane of the light beam 6 exists and rides onto the belt 38. With the belts 32 and 38 being held temporarily stationary, the portion of the object present in the space S is scanned by the light beam 6 reflected by the reflector 7, and the photodetector 9 receives the light transmitted through the object to produce an absorbance signal on a line L₄.

The motor 31 rotates the annular gantry 30 so that the light beam 6 irradiates the object 3 in all directions circumferentially of the object.

In the above-mentioned manner, it is possible to obtain a tomographic image of a desired portion of the object anywhere form the forward to the rear end of the object.

To describe the operation in further detail, the conveyor belt 32 conveys the object 3 placed thereon as far as that portion of the object which is to be sliced comes in the space S between the two belts 32 and 38, whereupon the belts 32 and 38 are temporarily stopped. With the annular gantry 30 held stationary at a certain position, the scanner 8 is operated to cause the reflector 7 fixed to the rotational shaft 8a of the scanner to swing one time, thereby causing the light beam 6 to scan the whole measuring area including the whole section of the object. When all absorbance signals resulting from the scanning have been taken, the annular gantry 30 is rotated about its own axis a predetermined angle and then temporarily held stationary, whereupon absorbance data are sampled in the same manner as mentioned above. The operation is repeated until the gantry 30 completes one rotation about the object 3, and all the data obtained are processed by a data processor 44, which conducts necessary calculations and operations to produce a tomographic image of the portion of the object being examined. A controller 45 controls the above-mentioned operation.

Figure 4:
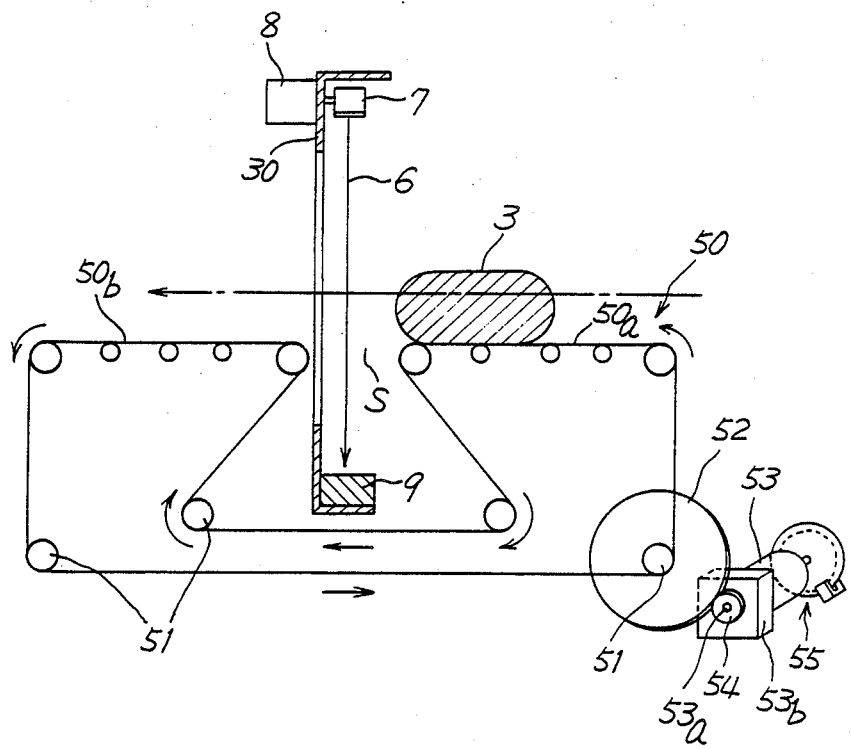
FIG. 4 is a schematic elevational view of a third embodiment of the invention.
Figure 7:
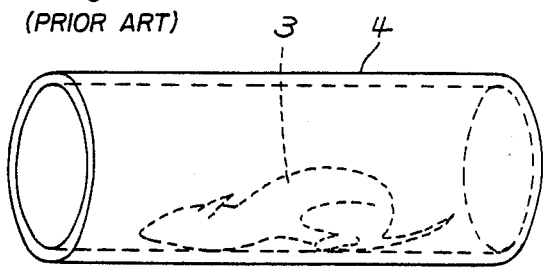
FIG. 7 is a perspective view of a conventional holder for holding an object to be examined.
Figure 5:
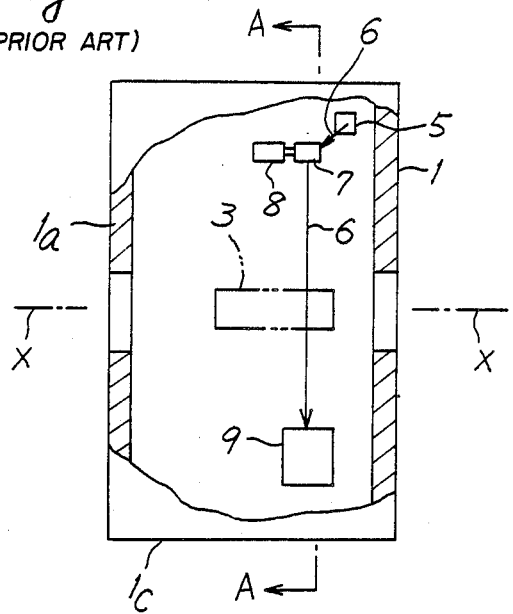
FIG. 5 is a schematic side view, partly cut away, of a conventional CT.
Figure 6:
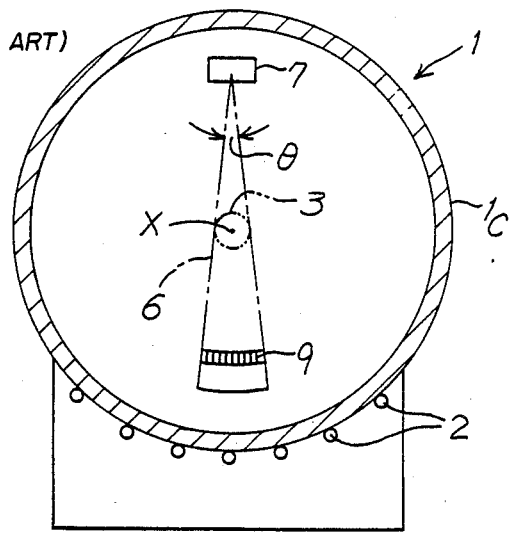
FIG. 6 is a sectional view taken along line A—A in FIG. 5.
Figure 8:
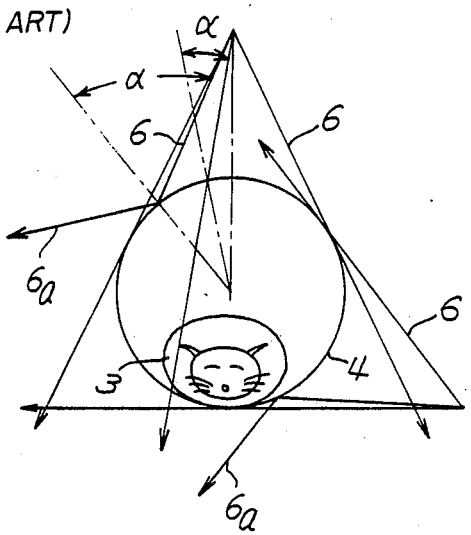
FIG. 8 is a schematic end view of the holder of FIG. 7 showing the relation between the holder and the scanning light beam.
Figure 9:
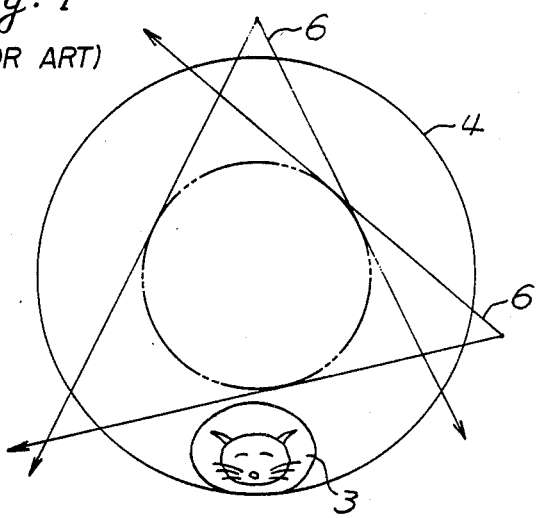
FIG. 9 is a schematic end view similar to FIG. 8 showing a larger holder.

FIG. 4 shows a third embodiment of the invention. In the embodiment of FIG. 3, the object introducing means and the object receiving means are separate means with the scanning plane interposed therebetween. In the embodiment of FIG. 4, a single endless conveyor belt 50 has an object introducing portion 50a at one side of the scanning plane and an object receiving portion 50b at the opposite side of the plane, with rollers 51 guiding the belt 50 so that the intermediate portion of the belt passes below the gantry 30.

Since the single belt is employed, a single driving mechanism suffices, which comprises a driving motor 53, a gear 54 fixed to the output shaft 53a of a reduction gear 53b connected to the motor and a gear 52 fixed to one of the rollers 51 and meshing with the gear 54. A position detector 55 is provided to detect the position of the conveyor belt 50 in a manner similar to the position detector 37 or 43 in the embodiment of FIG. 3.

In the third embodiment with the single conveyor belt 50, a single mechanism for driving the object holder suffices, with resulting simplification of the electrical circuitry and control system. The single belt 50 moves necessarily at the same speed in both the object introducing and receiving portions 50a and 50b, and there is no need for providing means for equalizing the running speeds of the two portions.

In the embodiments of FIGS. 3 and 4, since the two portions 50a and 50b of the conveyor belt 50 move synchronously, the position and width of the space S in which the scanning light beams passes is kept constant regardless of the movement of the belt and the object placed thereon, so that it is possible to measure a desired portion of the object continuously from the forward to the rear end thereof.

In accordance with the invention, since the object holder comprises two portions at the opposite sides of the scanning plane of the light beam, with an object to be examined being horizontally moved through the scanning plane perpendicularly thereto, only air except for the object exists in the space in which the scanning beam passes when measurement is conducted, so that it is possible to measure the object stably without any adverse influence of refraction or reflection of the scanning light beam on the results of measurement.

Since the object is supported at two positions at the opposite sides of the scanning plane, the object can be held more stably during measurement than if it were supported at one position like a cantilever.

What we claim is:
1. A computed tomograph comprising:
   (a) means for providing a beam of light in the visible and infrared regions;
   (b) means for holding an object to be examined;
   (c) means for scanning with said beam of light said object in a predetermined scanning plane;
   (d) photodetecting means for receiving said beam of light transmitted through said object to produce an electrical signal corresponding to the intensity of said transmitted light;
   (e) means for processing said electrical signal to produce a tomographic image of said object in said scanning plane;
   (f) said holding means comprising two separate portions arranged at the opposite sides of said scanning plane, each of said separate portions having a supporting surface at substantially the same level for supporting at least a portion of said object; and
   (g) means connected to said holding means for moving said holding means so that said object thereon moves perpendicularly to and through said scanning plane from one to the other side thereof;

(h) wherein said holding means comprises a first holding plate provided at one side of said scanning plane and a second holding plate provided at the opposite side of said scanning plane;

(i) wherein said moving means comprises a movable member fixed to one of said first and second holding plates, means for moving said movable member in a direction perpendicular to said scanning plane, and bearing means for supporting the other of said first and second holding plates slidably in a direction perpendicular to said scanning plane;

(j) wherein said moving means further includes first means for adjusting the position of said movable member with said one holding plate fixed thereto in a direction parallel with said scanning plane, and second means for adjusting the position of said bearing means with said other holding plate thereon in a direction parallel with said scanning plane.

2. The apparatus of claim 1, wherein one of said first and second holding plates is transparent to said light.

3. A computed tomograph comprising:
(a) means for providing a beam of light in the visible and infrared regions;
(b) means for holding an object to be examined;
(c) means for scanning with said beam of light said object in a predetermined scanning plane;
(d) photodetecting means for receiving said beam of light transmitted through said object to produce an electrical signal corresponding to the intensity of said transmitted light;
(e) means for processing said electrical signal to produce a tomographic image of said object in said scanning plane;
(f) said holding means comprising two separate portions arranged at the opposite sides of said scanning plane, each of said separate portions having a supporting surface at substantially the same level for supporting at least a portion of said object; and
(g) means connected to said holding means for moving said holding means so that said object thereon moves perpendicularly to and through said scanning plane from one to the other side thereof;
wherein said holding means comprises a single endless conveyor belt having a first surface portion arranged at one side of said scanning plane, a second surface portion arranged at the opposite side of said scanning plane and at the same level as said first surface portion, and an intermediate surface portion arranged between said first surface portion and said second surface portion; and
wherein said intermediate surface portion extends through said predetermined scanning plane and is disposed at a level below the level of the first surface portion and the second surface portion.

4. The apparatus of claim 3, wherein said moving means further includes means for detecting the position of said endless belt to produce a corresponding signal.

5. A device for holding an object to be examined in a computed tomograph wherein the object is scanned with a beam of light in a scanning plane and the light transmitted through the object is received by a photodetector to obtain a tomographic image of the object, said device comprising:
(a) two separate portions arranged at opposite sides of said scanning plane, each of said separate portions having a supporting surface at substantially the same level for supporting at least a portion of said object; and
(b) means connected to said holding means for moving said two separate portions so that said object thereon moves perpendicularly to and through said scanning plane from one to the other side thereof;
wherein one of said two separate portions comprises a first holding plate provided at one side of said scanning plane and the other of said two separate portions comprises a second holding plate provided at the opposite side of said scanning plane, and wherein said moving means comprises a movable member fixed to one of said first and second holding plates, and means for moving said movable member in a direction perpendicular to said scanning plane, and bearing means for supporting the other of said first and second holding plates slidably in a direction perpendicular to said scanning plane;
wherein said device further comprises first means for adjusting the position of said movable member with said one holding plate fixed thereto in a direction parallel with said scanning plane and second means for adjusting the position of said bearing means with said other holding plate thereon in a direction parallel with said scanning plane.

6. The device of claim 5, wherein one of said two separate portions comprises a first surface portion of a single endless conveyor belt arranged at one side of said scanning plane and the other of said two separte portions comprises a second surface portion of said same single conveyor belt arranged at the opposite side of said scanning plane and at the same level as said first surface portion, and wherein said moving means is connected to said single conveyor belt and includes means for detecting the position of said single endless conveyor belt to produce a control signal.

* * * * *